(12) United States Patent
Maki et al.

(10) Patent No.: US 9,216,213 B2
(45) Date of Patent: Dec. 22, 2015

(54) ADJUVANTED RABIES VACCINE WITH IMPROVED VISCOSITY PROFILE

(75) Inventors: Joanne L. Maki, Colbert, GA (US); Tricia Lynn Fry, Fort Collins, CO (US); Jerome Cornelius Hurley, Fort Collins, CO (US); Lowell Allen Miller, Greeley, CO (US)

(73) Assignees: MERIAL, INC., Duluth, GA (US); The United States of America As Represented By The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/451,667

(22) Filed: Apr. 20, 2012

(65) Prior Publication Data

US 2012/0269846 A1 Oct. 25, 2012

Related U.S. Application Data

(60) Provisional application No. 61/477,548, filed on Apr. 20, 2011.

(51) Int. Cl.
| | | |
|---|---|---|
| *A61K 39/205* | (2006.01) | |
| *A61P 31/14* | (2006.01) | |
| *A61K 39/00* | (2006.01) | |
| *C07K 14/145* | (2006.01) | |
| *C07K 14/115* | (2006.01) | |
| *A61K 39/285* | (2006.01) | |
| *C12N 15/39* | (2006.01) | |
| *C12N 15/863* | (2006.01) | |
| *A61K 39/12* | (2006.01) | |
| *A61K 39/39* | (2006.01) | |

(52) U.S. Cl.
CPC .............. *A61K 39/205* (2013.01); *A61K 39/12* (2013.01); *A61K 39/39* (2013.01); *A61K 2039/5256* (2013.01); *A61K 2039/542* (2013.01); *A61K 2039/55583* (2013.01); *C07K 14/145* (2013.01); *C12N 2710/24111* (2013.01); *C12N 2710/24141* (2013.01); *C12N 2710/24143* (2013.01); *C12N 2760/18034* (2013.01); *C12N 2760/20134* (2013.01)

(58) Field of Classification Search
CPC ... A61K 2300/00; A61K 45/06; A61K 9/006; A61K 39/12; A61K 39/3955; A61K 2039/525; A61K 39/285; A61K 2039/6075; A61K 35/76; A61K 39/275; C07D 417/14; C12N 7/00; C12N 2750/14134; C12N 2750/14334; C12N 15/86; C12N 2710/24143; C12N 2740/15034; C12N 2740/15043; C12N 2740/16043
See application file for complete search history.

(56) References Cited

U.S. PATENT DOCUMENTS

| | | | |
|---|---|---|---|
| 5,747,063 A | | 5/1998 | Languet et al. |
| 5,830,477 A | * | 11/1998 | Lathe et al. ................. 424/224.1 |
| 5,980,912 A | | 11/1999 | Podolski et al. |
| 6,024,953 A | * | 2/2000 | Lathe et al. ................... 424/93.2 |
| 2004/0037840 A1 | * | 2/2004 | Beier et al. ................. 424/185.1 |
| 2005/0282210 A1 | | 12/2005 | Maki |
| 2010/0129403 A1 | * | 5/2010 | Bonnefoy et al. .......... 424/232.1 |
| 2010/0303838 A1 | * | 12/2010 | Silvestre et al. ............ 424/184.1 |

FOREIGN PATENT DOCUMENTS

| | | | |
|---|---|---|---|
| WO | WO 2006002160 A1 | | 1/2006 |
| WO | WO 2008105934 A2 | * | 9/2008 |

OTHER PUBLICATIONS

Cliquet F, Barrat J, Guiot AL, Caël N, Boutrand S, Maki J, Schumacher CL. Efficacy and bait acceptance of vaccinia vectored rabies glycoprotein vaccine in captive foxes (Vulpes vulpes), raccoon dogs (Nyctereutes procyonoides) and dogs (Canis familiaris). Vaccine. Aug. 26, 2008;26(36):4627-38. Epub Jul. 11, 2008.*
Han HD, Song CK, Park YS, Noh KH, Kim JH, Hwang T, Kim TW, Shin BC. A chitosan hydrogel-based cancer drug delivery system exhibits synergistic antitumor effects by combining with a vaccinia viral vaccine. Int J Pharm. Feb. 28, 2008;350(1-2):27-34. Epub Aug. 19, 2007.*
Verheul RJ, Amidi M, van der Wal S, van Riet E, Jiskoot W, Hennink WE. Synthesis, characterization and in vitro biological properties of O-methyl free N,N,N-trimethylated chitosan. Biomaterials. Sep. 2008;29(27):3642-9. Epub Jun. 16, 2008.*
Hagenaars N, Mania M, de Jong P, Que I, Nieuwland R, Slütter B, Glansbeek H, Heldens J, van den Bosch H, Löwik C, Kaijzel E, Mastrobattista E, Jiskoot W. Role of trimethylated chitosan (TMC) in nasal residence time, local distribution and toxicity of an intranasal influenza vaccine. J Control Release. May 21, 2010;144(1):17-24. Epub Jan. 25, 2010.*
Verheul RJ, Amidi M, van Steenbergen MJ, van Riet E, Jiskoot W, Hennink WE. Influence of the degree of acetylation on the enzymatic degradation and in vitro biological properties of trimethylated chitosans. Biomaterials. Jun. 2009;30(18):3129-35. Epub Mar. 31, 2009.*
Verheust C, Goossens M, Pauwels K, Breyer D. Biosafety aspects of modified vaccinia virus Ankara (MVA)-based vectors used for gene therapy or vaccination. Vaccine. Mar. 30, 2012;30(16):2623-32. Epub Feb. 17, 2012.*
Pastoret PP, Vanderplasschen A. Poxviruses as vaccine vectors. Comp Immunol Microbiol Infect Dis. Oct. 2003;26(5-6):343-55.*
Mourya Vk, Inamdar NN. Trimethyl chitosan and its applications in drug delivery. J Mater Sci Mater Med. 2009 May;20(5):1057-79. Epub Dec. 27, 2008*

(Continued)

*Primary Examiner* — Benjamin P Blumel
*Assistant Examiner* — Rachel Gill
(74) *Attorney, Agent, or Firm* — Judy Jarecki-Black; Chad Kitchen; Merial, Inc.

(57) ABSTRACT

The present invention relates to adjuvanted recombinant anti-rabies vaccines and the oral administration of such vaccines to raccoons and other wildlife. Advantageously, the anti-rabies vaccine may comprise a recombinant vaccinia virus containing a rabies glycoprotein gene. The invention encompasses methods of vaccinating raccoons and other wildlife by administration of an anti-rabies vaccines which may comprise a recombinant vaccinia virus containing a rabies glycoprotein gene, in combination with an adjuvant which increases both vaccine viscosity and efficacy. The invention provides effective oral recombinant vaccines used in oral rabies vaccination (ORV) programs for wildlife, effective at protecting raccoons, gray foxes, coyotes, and other animals.

12 Claims, 4 Drawing Sheets

(56) References Cited

OTHER PUBLICATIONS

Hermann JR, Fry AM, Siev D, Slate D, Lewis C, Gatewood DM. Stability of vaccinia-vectored recombinant oral rabies vaccine under field conditions: a 3-year study. Can J Vet Res. Oct. 2011;75(4):278-84.*

He P, Davis SS, Illum L. Sustained release chitosan microspheres prepared by novel spray drying methods. J Microencapsul. May-Jun. 1999;16(3):343-55.*

Truter EM. 2005. "Chitosan Derived Formulations and EMZALOID™ Technology for Mucosal Vaccination against Diphtheria: Nasal Efficacy in Mice." Dissertation. North-West University. Kotze AF, Van der Merwe SM, Supervisors.*

Lu Z, Steenekamp JH, Hamman JH. Cross-linked cationic polymer microparticles: effect of N-trimethyl chitosan chloride on the release and permeation of ibuprofen. Drug Dev Ind Pharm. Mar. 2005;31(3):311-7.*

Greenspan NS, Di Cera E. Defining epitopes: It's not as easy as it seems. Nat Biotechnol. Oct. 1999;17(10):936-7.* van der Lubben IM, van Opdorp FA, Hengeveld MR, Onderwater JJ, Koerten HK, Verhoef JC, Borchard G, Junginger HE. Transport of chitosan microparticles for mucosal vaccine delivery in a human intestinal M-cell model. J Drug Target. Sep. 2002;10(6):449-56.*

Chen F, Zhang ZR, Yuan F, Qin X, Wang M, Huang Y. In vitro and in vivo study of N-trimethyl chitosan nanoparticles for oral protein delivery. Int J Pharm. Feb. 12, 2008;349(1-2):226-33. Epub Aug. 2, 2007.*

Jain S, Sharma RK, Vyas SP. Chitosan nanoparticles encapsulated vesicular systems for oral immunization: preparation, in-vitro and in-vivo characterization. J Pharm Pharmacol. Mar. 2006;58(3):303-10.*

Tian JY, Sun XQ, Chen XG. Formation and oral administration of alginate microspheres loaded with pDNA coding for lymphocystis disease virus (LCDV) to Japanese flounder. Fish Shellfish Immunol. May 2008;24(5):592-9. Epub Feb. 1, 2008.*

Li XY, Li X, Kong XY, Shi S, Guo G, Zhang J, Luo F, Zhao X, Wei YQ, Qian ZY, Yang L. Preparation of N-trimethyl chitosan-protein nanoparticles intended for vaccine delivery. J Nanosci Nanotechnol. Aug. 2010;10(8):4850-8.*

Bowersock TL and Martin S. In M.J. Rathbone, R. Gurn, eds. Controlled Release Veterinary Drug Delivery: Biological and Pharmaceutical Considerations. M.J. Rathbone, R. Gurny Elsevier, Jul. 20, 2000—Science-392. Chapter 10: Controlled release vaccines in veterinary medicine. pp. 269-311.*

Hicks DJ, Fooks AR, Johnson N. Developments in rabies vaccines. Clin Exp Immunol. Sep. 2012;169(3):199-204.*

Mateu MG, et. al. Eur J Immunol. Jun. 1992;22(6):1385-9.*

Fry TL, Nash P, Hurley J, Dunbar M. Evaluation of Potential Mucosal Adjuvants for Enhancing Delivery of an Oral Rabies Vaccine to Wildlife. RITA 2010 Program Poster. Displayed in "RITA" conference in Guadalajara, Mexico, Oct. 17-22, 2010.*

Rauw F. et al. "Improved vaccination against Newcastle disease by an in ovo recombinant HVT-ND combined . . .", VACCINE, vol. 28, No. 3, Jan. 8, 2010, pp. 823-833.

Mackowiak M. et al. Vaccination of Wildlife against Rabies: Successful Use of a Vectored Vaccine Obtained by Recombinant Technology. Adv Vet Med. 1999;41:571-83.

Grosenbaugh Deborah A et al. "Rabies challenge of captive striped skunks (*Mephitis mephitis*) following oral administration of a live vaccinia-vectored rabies vaccine" J Wildlife Dis 2007;43(1):124-8).

Baudner Barbara C et al. Mucosal adjuvants and delivery systems for oral and nasal vaccination. Drugs of the Future 2004; 29(7):721-732.

Van Der Merwe S M et al: "Trimethylated chitosan as polymeric absorption enhancer for improved peroral delivery of peptide drugs", Eur. J. Pharm. and Biopharm, 2004.

Bal SM. et al. Efficient induction of immune responses through intradermal vaccination with N-trimethyl chitosan containing antigen formulations, 2010.

Patel et al. Formulation and evaluation of mucoadhesive glipizide microspheres. AAPS PST (2005).

Linhart et al. New flavor-coated sachet bait . . . J. Wildlife Dis., 2002 (363-377).

Van Der Lubben et al., Chitosan for mucosal vaccination. Adv. Drug. Deliv. Rev. 2001; 52: 139-144.

Van Der Lubben et al. Chitosan and its derivatives in mucosal drugs and vaccine delivery. European J. Pharmaceutical Sciences 2001; 14:201-207.

Blanton JD. et al. Vaccine 25 (2007) 7296-7300.

Vajdy M. et al. Mucosal adjuvants and delivery systems for protein-, DNA- and RNA-based vaccines. Immunology and Cell Biology (2004) 82, 617-627.

RITA 2010 Program Poster—displayed at "RITA" conference in Guadalajara, Mexico. Oct. 17-22, 2010. Applicants understand the follow as regards this poster presentation: 1) Posters were displayed for only a few hours; 2) Attendees generally work on *issues related to rabies*, but the contents of this poster would not have been within the realm of typical research and/or interest for most of the conference participants. 3) The poster was displayed in English and many participants were non-English speaking. 4) It is very unlikely anyone copied this poster.

* cited by examiner

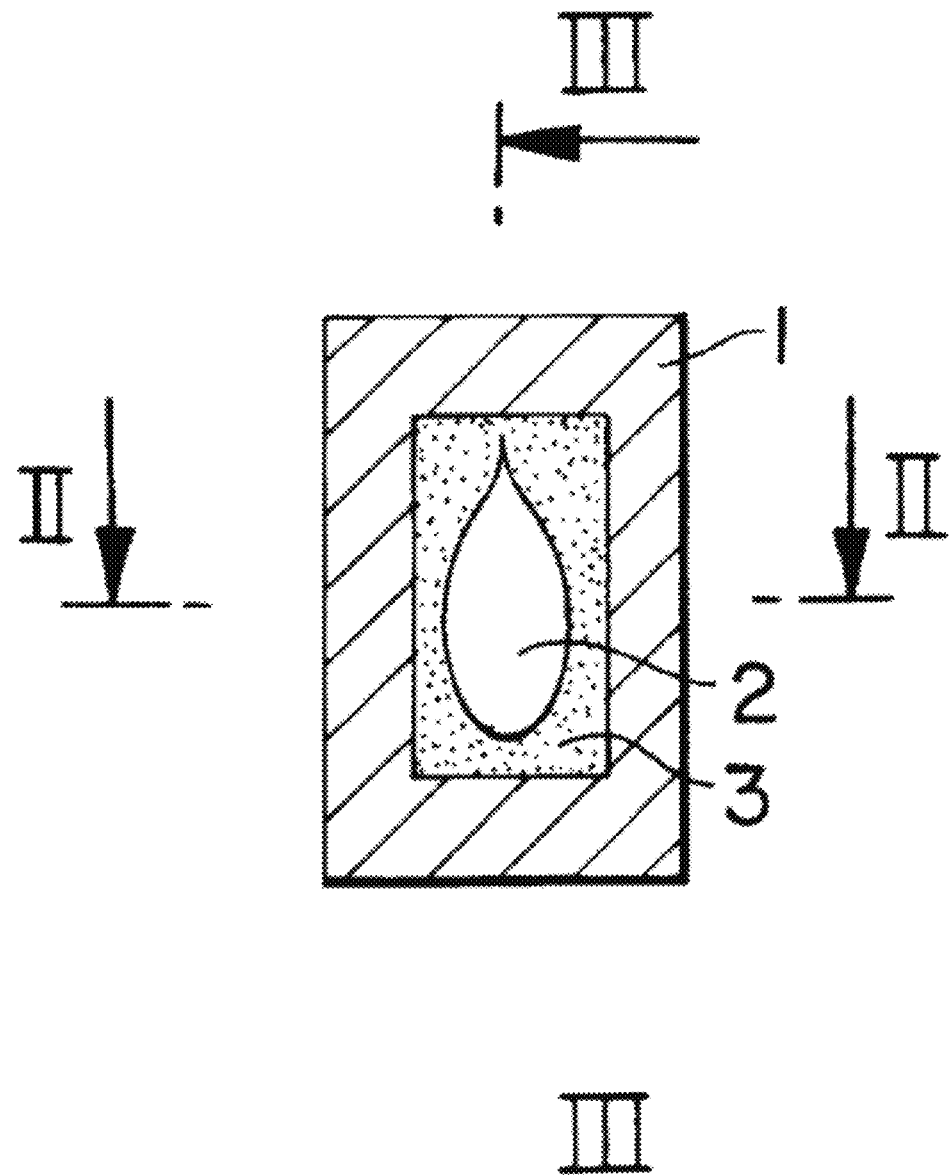

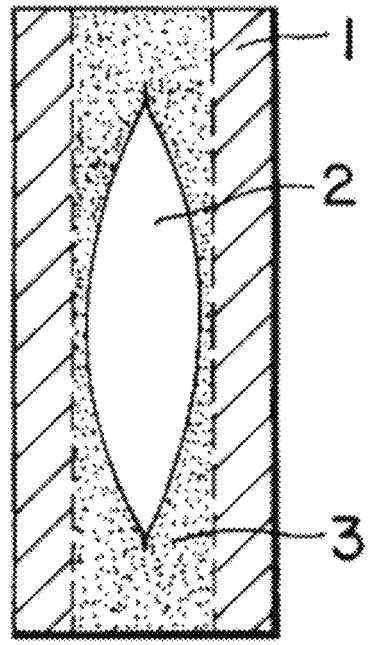
FIG. 2B - PRIOR ART
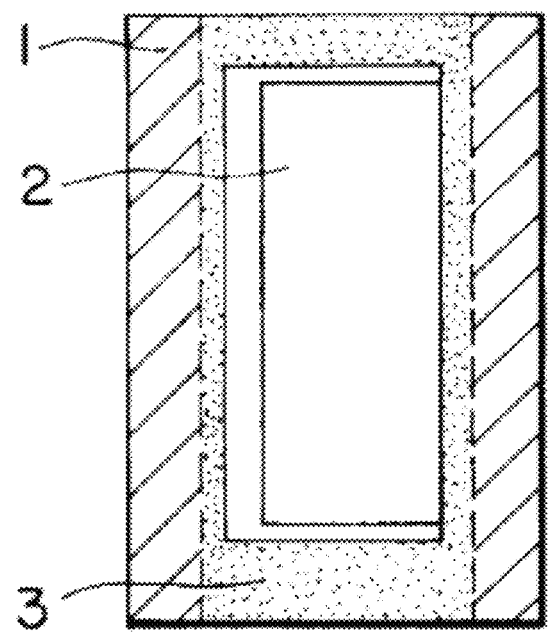
FIG. 2C - PRIOR ART

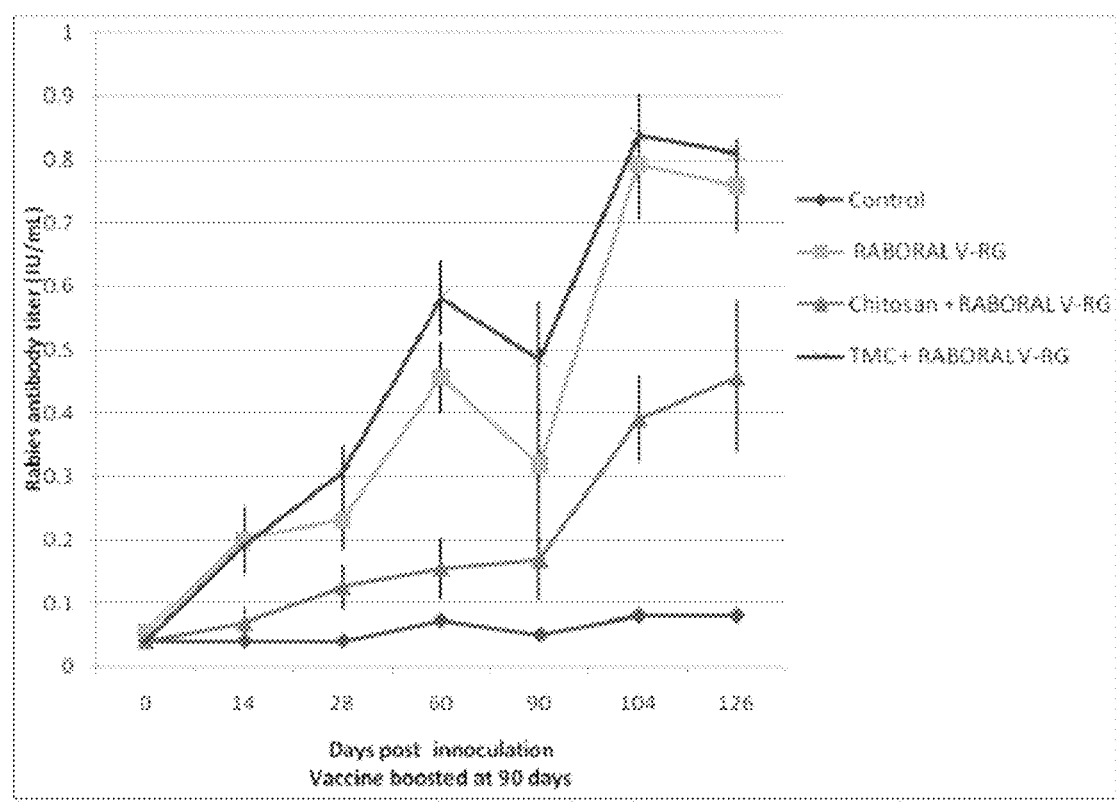
FIG. 3 Average rabies virus neutralizing antibodies (IU/mL) over the course of the study

ADJUVANTED RABIES VACCINE WITH IMPROVED VISCOSITY PROFILE

INCORPORATION BY REFERENCE

This application claims priority to U.S. provisional patent application No. 61/477,548, filed Apr. 20, 2011, the disclosure of which is herein incorporated by reference in its entirety.

FIELD OF THE INVENTION

The present invention relates to adjuvanted rabies vaccines having improved viscosity profiles.

BACKGROUND

Rabies is a disease that can occur in all warm-blooded species and is caused by rabies virus. Infection with rabies virus followed by the outbreak of the clinical features in nearly all instances results in death of the infected species. In Europe, the USA and Canada wild life rabies still exists and is an important factor in the cause of most human rabies cases that occur. On the other hand, urban rabies constitutes the major cause of human rabies in developing countries.

Rabies virus is a non-segmented negative-stranded RNA virus of the Rhabdoviridae family. Rabies virus virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in rabies virus and additionally is the main target for the host immune system. The amino acid region at position 330 to 340 (referred to as antigenic site III) of the G protein has been identified to be responsible for the virulence of the virus, in particular the Arg residue at position 333. All rabies virus strains have this virulence determining antigenic site III in common.

RABORAL V-RG® was developed as an alternative rabies vaccine by Merial, Ltd. As an alternative rabies vaccine that proved to have the unique and novel attribute of being effective by the oral route (reviewed by Mackowiak et al., Adv Vet Med. 1999; 41:571-83). The vaccine comprises a modified live vaccinia virus containing the rabies surface glycoprotein gene inserted in its genome. The first experimental use of the recombinant vaccine in wildlife was initiated in Europe. The vaccine was contained within a plastic sachet surrounded by an edible bait and deployed into areas known to contain rabies-infected red fox populations. These campaigns resulted in a dramatic reduction in rabies cases in red foxes and the use of RABORAL V-RG® was considered a success. RABORAL V-RG® was also found to be effective in causing a reduction in rabies in raccoons, coyotes and red foxes (reviewed by Mackowiak et al., Adv Vet Med. 1999; 41:571-83), as well as skunks and mongooses (US2005/0282210A1, Maki J L et al, Merial Limited; Grosenbaugh D A, Maki J L et al. J Wildlife Dis 2007; 43(1):124-8).

Despite the success of oral vaccination of wildlife, Rabies continues to pose a significant health threat, killing over 55,000 people annually and necessitating prophylactic treatment of over 15 million people post-exposure each year (WHO: Rabies vaccines). One of the goals of the USDA-APHIS Wildlife Services National Rabies Management Program (WS NRMP) has been to control and eventually eliminate terrestrial rabies in the United States. In contrast to some other parts of the world, the primary reservoir for the virus in the United States is wildlife. In an attempt to achieve rabies eradication, oral rabies vaccines are distributed by hand and aircraft in most states east of the Appalachian Mountains as well as portions of Ohio, Arizona, and Texas. It has been estimated that a vaccination rate of 70% is considered sufficient to break disease transmission cycles (Hethcote, H W et al. 1978). Presently, it is estimated that Oral Rabies Vaccination (ORV) programs in the U.S. successfully vaccinate only 30% of raccoons (Slate, D. et al. 2009), while vaccination rates have been sufficiently high to eradicate gray fox and canine rabies in foxes and coyotes, respectively in Texas (Fearneyhough, M G et al., 1998; Sidwa, T J et al., 2005).

The ORV program led by WS NRMP currently uses the vaccine, RABORAL V-RG® (Merial Ltd., Athens, Ga., described above) in its vaccination campaigns. Currently, RABORAL V-RG® is delivered in a liquid form that is contained within a flavor-coated, plastic sachet. Under optimal conditions, when the sachet is pierced by an animal bite the vaccine is released into the buccal cavity and coats the mucosal lining of the mouth. There the recombinant virus expressing the rabies glycoprotein attaches and enters host cells, triggering an immune response. Previous studies have shown that an approximate dose of 107.7 TCID50/1.5 mL of RABORAL V-RG® is necessary to protect a majority of raccoons from challenge with a wild-type rabies strain (Grosenbaugh, D A et al. 2007). However, because the vaccine is delivered in a liquid form, it is often spilled or rejected by the animal, there are concerns related to the amount of RABORAL V-RG® an animal actually ingests (Grosenbaugh, D A et al., 2007; Jojola, S M et al. 2007).

There are at least two potential mechanisms to increase the effectiveness of orally administered RABORAL V-RG®: increase the viscosity of the vaccine and/or include an adjuvant. Adjuvants are compounds that, when combined with a vaccine antigen, increase the immune response to the vaccine antigen as compared to the response induced by the vaccine antigen alone. Among strategies that promote antigen immunogenicity are those that render vaccine antigens particulate, those that polymerize or emulsify vaccine antigens, methods of encapsulating vaccine antigens, ways of increasing host innate cytokine responses, and methods that target vaccine antigens to antigen presenting cells (Nossal, 1999, In: Fundamental Immunology. Paul (Ed.), Lippincott-Raven Publishers, Philadelphia, Pa.; Vogel and Powell, 1995, In: Vaccine Design. The Subunit and Adjuvant Approach. Powell and Newman (Eds.), Plenum Press, NY, N.Y. p. 141). Because of the essential role adjuvants play in improving the immunogenicity of vaccine antigens, the use of adjuvants in the formulation of vaccines has been virtually ubiquitous (Nossal, 1999, supra; Vogel and Powell, 1995, supra; see also PCT publication WO 97/18837, the teachings of which are incorporated herein by reference).

Conventional adjuvants, well-known in the art, are diverse in nature. They may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine antigen as compared to the response induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra). In sum, adjuvants generally appear to exert their effects in at least one of five ways: 1) facilitate antigen uptake, transport and presentation in the lymph nodes, 2) prolong antigen presentation, 3) signal pathogen-recognition receptors (PRRs) expressed on innate immune cells, 4) cause damage or stress to cells, which signals an immune response, and 5) induce a preferential Th1 or Th2 response (Schijns V E et al. 2007).

Some adjuvants have demonstrated particular adjuvanting utility, in part, by promoting improved absorption through mucosal linings. Some examples include MPL, LTK63, toxins, PLG microparticles and several others (Vajdy, M. Immunology and Cell Biology (2004) 82, 617-627), but many of these are not practical to employ as part of a wildlife vaccination strategy due to the high expense and/or poor stability in the field. One reasonably affordable mucosal adjuvant, chitosan (Van der Lubben et al. 2001; Patel et al. 2005; Majithiya et al. 2008; U.S. Pat. No. 5,980,912), has demonstrated some efficacy when used in certain human vaccines, but the polymer has not previously been successfully combined with veterinary biologics. Persons skilled in the vaccine development arts understand that effective adjuvant/antigen/host combinations are unpredictable and require significant experimentation to derive. See for example Edelman, "An Update on Vaccine Adjuvants in Clinical Trial," Aids Research and Human Retroviruses 8(8):1409-1411 (1992); McElrath, "Selection of potent immunological adjuvants for vaccine construction," seminars in Cancer Biology 6:375-385 (1995); Aucouturier et al., "Adjuvants designed for veterinary and human vaccines," Vaccine 19:2666-2672 (2001); East et al., "Adjuvants for New Veterinary Vaccines," Chapter 1 in Progress in Vaccinology, vol. 4 Veterinary Vaccines, Springer Verlag, NY 1993, pp 1-28; Altman et al., "Immunomodifiers in Vaccines," Advances In Veterinary Science and Comparative Medicine 33:301-343 (1989); and Willson et al., "Tissue Reaction and Immunity in Swine Immunized with *Actinobacillus pleuropneumoniae* Vaccines," Can J Vet Res 59:299-305 (1995).

In view of the current suboptimal vaccination of wildlife against pathogens such as rabies, there is real and long-felt need for an adjuvanted vaccine bait that can be widely distributed at reduced cost and increased efficacy. An ideal adjuvanted bait should 1) be safe, inexpensive and easy to formulate, 2) reduce the amount of antigen dose required to achieve effective protection, 3) be relatively more viscous, to reduce loss/spillage, and 4) be stable in the environment long enough for the animals to become effectively vaccinated.

SUMMARY OF THE INVENTION

The invention is based, in part, on the unexpected and surprising result that RABORAL V-RG® formulated with specific variants of chitosan is effective for the oral vaccination of wildlife, including raccoons. The invention further contemplates other formulations comprising antigens and chitosans, wherein the chitosans provide improved vaccine efficacy by acting as vaccine adjuvants, including increasing the viscosity of oral vaccine formulations, thereby promoting improved mucosal absorption and/or transport. In an embodiment, the effective dose is significantly lower than that required in absence of the inventive adjuvanting chitosans. In another embodiment, at least one other antigen may be added to the inventive formulations.

The invention relates also to a method for screening candidate adjuvants in vitro, to reduce the testing of compounds that have deleterious effects on the antigens. In particular, the instant disclosure provides in vitro methods to assess whether/to what extent candidate adjuvants exert virucidal activity on the vector component of vaccines. In an embodiment, only adjuvants with no or little virucidal effects are advanced to more costly and time-consuming animal studies.

In an embodiment, candidate adjuvants are combined with vaccine vector component and allowed to incubate on cultured cells, including but not solely, Vero, CEF, or any cell suitable or routinely employed for measuring the effective titer of recombinant viral vectors.

The invention further relates to a method of eliciting an immune response in a wild animal, including raccoons and other wildlife, which may comprise administering a composition which may comprise a viral vector which may comprise a rabies surface glycoprotein gene inserted into the viral vector genome in an amount effective for eliciting an immune response in the raccoon or other wildlife. The method may include using compositions comprising chitosan derivatives.

In a first embodiment the present invention provides for a novel adjuvanted rabies vaccine, or vaccine bait for use in the wild, including, but not limited to, forests, wetlands, and plains.

In one embodiment, the vector may comprise a modified live vaccinia virus. In another embodiment, the rabies surface glycoprotein gene may be rabies glycoprotein G, which is derived from an ERA strain in one embodiment.

In another embodiment, the vaccinia virus or the vaccinia virus vector may be a Copenhagen strain or a derivative thereof. In another embodiment, the vaccinia virus or the vaccinia virus vector may have a tk– phenotype. In an advantageous embodiment, the vaccinia virus or the vaccinia virus vector may be a Copenhagen strain (or a derivative thereof) and has a tk– phenotype.

In an advantageous embodiment, the modified live vaccinia virus may be RABORAL V-RG®.

In another embodiment, administration of the above-described compositions may be oral and be accomplished via a bait drop. In one embodiment, the bait drop may comprise a hollow plastic packet. In another embodiment, the composition may be inserted in the hollow polymer cube. The bait drop may also comprise a coated sachet.

In an embodiment, the coated sachet may be as described in Linhart et al., Journal of Wildlife Diseases, 2002, where RABORAL V-RG® was delivered using different baits with varying geometrical shape and flavor (FIG. 1).

In yet another embodiment, the composition may be provided as described in U.S. Pat. No. 5,747,063. The vaccine may take the form indicated in FIGS. 2A-2C, wherein it comprises an envelope (1), which comprises in admixture one or more craved for materials and one or more substances agglomerating the craved for materials, the envelope possessing a high mechanical and thermal resistance and being previously formed into a hollow shape appropriate for consumption by the animal and defining an internal volume. such internal volume being filled by a craved for binder (3) and comprising the active principle (2). the binder closely conforming the internal shape of the envelope (1) in order to provide a continuity between the envelope (1) and the active principle (2), and further comprising the instantly disclosed adjuvants.

In another embodiment, the vaccination efficacy achieved using RABOARL V-RG formulated with an adjuvant according to the disclosure is significantly increased relative to vaccination efficacy achieved using RABORAL V-RG® formulated without the adjuvant.

In yet another embodiment, administration of the above-described compositions may be nasal or through contact with the nasal mucosa.

The invention also encompasses a method for inducing an immunological or protective immune response in wildlife, including but not solely, raccoon, coyote, fox, skunk or mongoose, which may comprise administering a composition which may comprise a viral vector which may comprise a rabies surface glycoprotein gene inserted into the viral vector genome in an amount effective for eliciting an immune response in the wild animal.

In one embodiment, the vector may comprise a modified live vaccinia virus. In another embodiment, the rabies surface glycoprotein gene may be rabies glycoprotein G, which is derived from an ERA strain in one embodiment.

In another embodiment, the vaccinia virus or the vaccinia virus vector may be a Copenhagen strain or a derivative thereof. In another embodiment, the vaccinia virus or the vaccinia virus vector may have a tk– phenotype. In an advantageous embodiment, the vaccinia virus or the vaccinia virus vector may be a Copenhagen strain (or a derivative thereof) and has a tk– phenotype.

In an embodiment, the modified live vaccinia virus may be RABORAL V-RG® formulated with trimethylated chitosan.

The invention also provides for a kit for performing any of the above described methods comprising the any of the above described compositions and optionally, instructions for performing the method.

Another embodiment of the present invention provides for a stable, safe and easily administerable vaccine. In an embodiment, the vaccine is a wildlife bait that is consumed by animals including, but not solely, raccoons, coyotes, foxes, rabbits, bats, squirrels, canines, and felines.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 2A represents a transversal cross-section of a vaccine bait drop;

FIG. 2B represents a longitudinal cross-section along line II-II of FIG. 2A;

FIG. 2C represents a longitudinal cross-section along line III-III of FIG. 2B;

FIG. 3 provides graph of average rabies virus neutralizing antibodies (IU/mL) over the course of the study, with error bars identifying standard deviation.

DETAILED DESCRIPTION OF THE INVENTION

Figure 1:
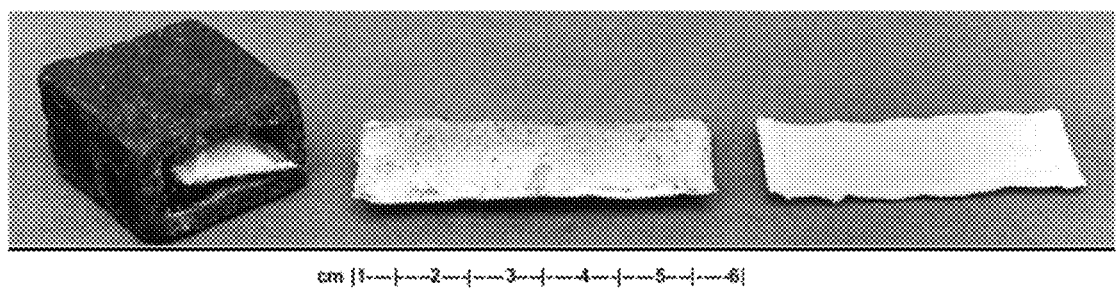
FIG. 1 provides representative images of a fish meal polymer bait on left (2.0×3.5×3.5 cm, 26 g); a sachet bait in center (0.5×2.0×6.0 cm, ~3.8 g); and right, a typical sachet that has been chewed, emptied of vaccine, and discarded by a raccoon.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

For convenience, certain terms employed in the Specification, Examples, and appended Claims are collected here.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is also noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

As used herein, the term "animal" includes all vertebrate animals including humans. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (i.e., different isolates of Rabies virus serotypes), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity, as compared with its efficacy in absence of the adjuvant. The mechanism of how adjuvants operate is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant, and adjuvants disclosed in U.S. Pat. No. 7,371,395 to Merial Limited, which are herein incorporated by reference in their entirety), *Corynebacterium parvum, Bacillus Calmette Guerin,* aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N',N'-bis(2-hydroxyethyl)-propanediamine), paraffin oil, muramyl dipeptide and the like.

As used herein, the term "emulsion" refers to a combination of at least two substances, wherein a first substance is dispersed in a second substance in which the first substance is insoluble. One example of an emulsion of the present invention is an oil phase dispersed in an aqueous phase.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The term "purified" as used herein does not require absolute purity; rather, it is intended as a relative term. Thus, for example, a purified immunogen preparation, such as protein or inactivated virus, is one in which the immunogen is more enriched than the immunogen is in its natural environment. An immunogen preparation is herein broadly referred to as "purified" such that the immunogen represents at least 60%, at least 70%, at least 80%, at least 90%, at least 95%, or at least 98%, of the total immunogen content of the preparation. A "crude preparation", which represents the lowest degree of purification, may contain as little as less than 60%, lest than 20%, less than 10%, less than 5%, or less than 1% of immunogenic components.

The term "highly purified" as used herein is intended to suggest a "higher degree of purity" as compared to the term "moderately purified". This "higher degree of purity" can include, but is in no way limited to, reduced percentages of contaminants, in an immunological preparation that has been "highly purified" versus an immunological preparation that has been "moderately purified". As discussed herein, "highly purified" immunological preparations will have the lowest to undetectable percentages of contaminants that can cause: reduced desired immune response, increased undesired immune response (e.g. hypersensitivity reaction), or reduced formulation stability. Similarly, an immunological preparation that has been "moderately purified" contains relatively reduced percentages of contaminants versus an immunological preparation that has been "minimally purified", which likewise, has reduced percentages of contaminants versus a preparation designated a "crude preparation".

Contaminants in an immunological preparation can include, but are in no way limited to, substances that contribute negatively to an immunological composition according to the present invention. One of several examples of a contaminant contributing negatively would be a contaminant that reduces the ability of an immunological composition of the present invention to elicit an immune response in animals.

Varying levels of purity (e.g. "highly purified", "moderately purified", and the like) can be achieved using various methods. For example, a combination of chromatography and size exclusion gel filtration can result in a "highly purified" or "moderately purified" immunological preparations. Differences in source/type of immunogens, as well as slight variations in purification procedures can significantly affect the final degree of immunogen purity. In general, as used herein, immunological preparations having the lowest to highest percentage of contaminants will be described as 1) "highly purified, 2) "moderately purified", 3) "minimally purified", 4) "crude preparation", respectively. A "highly purified" preparation will have the lowest level across all types of contaminants. A "moderately purified" preparation will have relatively low levels of most types of contaminants, but may have one type of contaminant in higher abundance than would be observed for a comparable "highly purified" preparation. Likewise, a "minimally purified preparation" will have relatively low levels of some types of contaminants, but may have more than one type of contaminant in higher abundance than a comparable "moderately purified" preparation. As expected, a "crude preparation" has the highest level of contaminants, across all contaminant types, as compared to the other types of preparations discussed herein.

In another embodiment, the rabies glycoprotein is any rabies glycoprotein with a known protein sequence, such as rabies virus glycoprotein G. such as the protein sequences in or derived from the nucleotide sequences in Marissen et al., J. Virol. April 2005; 79(8):4672-8; Dietzschold et al., Vaccine. Dec. 9, 2004; 23(4):518-24; Mansfield et al., J Gen Virol. November 2004; 85(Pt 11):3279-83; Sato et al., J Vet Med. Sci. July 2004; 66(7):747-53; Takayama-Ito et al., J. Neurovirol. April 2004; 10(2):131-5; Li et al., Zhongguo Yi Xue Ke Xue Yuan Xue Bao. December 2003; 25(6):650-4; Hemachudha et al., J Infect Dis. Oct. 1, 2003; 188(7):960-6; Kankanamge et al., Microbiol Immunol. 2003; 47(7):507-19; Maillard et al., Virus Res. June 2003; 93(2):151-8; Irie et al. Microbiol. Immunol. 2002; 46(7):449-61; Langevin et al., J Biol. Chem. Oct. 4, 2002; 277(40):37655-62; Maillard and Gaudin, J Gen Virol. June 2002; 83(Pt 6):1465-76; Holmes et al., Virology. Jan. 20, 2002; 292(2):247-57; Mebatsion, J. Virol. December 2001; 75(23):11496-502; Zhang et al., Zhonghua Shi Yan He Lin Chuang Bing Du Xue Za Zhi. September 2000; 14(3):281-4; Ray et al., Clin Exp Immunol. July 2001; 125(1):94-101; Morimoto et al., Vaccine. May 14, 2001; 19(25-26):3543-51; Morimoto et al., J Neurovirol. October 2000; 6(5):373-81; Bourhy et al., J Gen Virol. October 1999; 80 (Pt 10):2545-57; Kissi et al., J Gen Virol. August 1999; 80 (Pt 8):2041-50; Nakahara et al., Microbiol Immunol. 1999; 43(3):259-70; Matthews et al., J Gen Virol. February 1999; 80 (Pt 2):345-53; Tuffereau et al., EMBO J. Feb. 15, 1998; 17(24):7250-9; Jallet et al. J. Virol. January 1999; 73(1):225-33; Wloch et al., Hum Gene Ther. Jul. 1, 1998; 9(10):1439-47; Mellquist et al., Biochemistry. May 12, 1998; 37(19):6833-7; Morimoto et al., Proc Natl Acad Sci USA. Mar. 17, 1998; 95(6):3152-6; Coll, Arch Virol. 1997; 142 (10):2089-97; Bracci et al., Blood. Nov. 1, 1997; 90(9):3623-8; Gaudin et al., J Virol. November 1996; 70(11):7371-8; Morimoto et al., Proc Natl Acad Sci USA. May 28, 1996; 93(11):5653-8; Mebatsion et al., Cell. Mar. 22, 1996; 84(6): 941-51; Shakin-Eshleman et al., J Biol. Chem. Mar. 15, 1996; 271(11):6363-6; Nadin-Davis et al., J Virol Methods. March 1996; 57(1):1-14. Erratum in: J Virol Methods Apr. 26, 1996; 58(1-2):209; Wojczyk et al., Protein Exp. Purif. March 1996; 7(2):183-93; Suzuki et al., J Gen Virol. December 1995; 76 (Pt 12):3021-9; Raux et al., Virology. Jul. 10, 1995; 210(2): 400-8; Kasturi et al., J Biol. Chem. Jun. 16, 1995; 270(24): 14756-61; Otvos et al., Biochim Biophys Acta. May 29, 1995; 1267(1):55-64; Mebatsion et al., J Virol. March 1995; 69(3): 1444-51; Wojczyk B, Shakin-Eshleman S H, Doms R W, Xiang Z Q, Ertl H C, Wunner W H, Spitalnik, Biochemistry. Feb. 28, 1995; 34(8):2599-609; Ravkov et al., Virology. Jan. 10, 1995; 206(1):718-23; Ni et al., Microbiol Immunol. 1995; 39(9):693-702; Coll, Arch Virol. 1995; 140(5):827-51; Grabko et al., Dokl Akad Nauk. July 1994; 337(1):117-21; Sakamoto et al., Virus Genes. January 1994; 8(1):35-46; Fodor et al., Arch Virol. 1994; 135(3-4):451-9; Ito et al., Microbiol Immunol. 1994; 38(6):479-82; Shakin-Eshleman et al., Biochemistry. Sep. 14, 1993; 32(36):9465-72; Morimoto et al., Virology. August 1993; 195(2):541-9; van der Heijden et al., J Gen Virol. August 1993; 74 (Pt 8):1539-45; Nishihara et al., Gene. Jul. 30, 1993; 129(2):207-14; Rustici et al., Biopolymers. June 1993; 33(6):961-9; McColl et al., Aust Vet J. March 1993; 70(3):84-9; Bai et al., Virus Res. February 1993; 27(2):101-12; Nishihara et al., Nippon Rinsho. February 1993; 51(2):323-8; Bracci et al., FEBS Lett. Oct. 19, 1992; 311(2):115-8; Tuchiya et al., Virus Res. Sep. 1, 1992; 25(1-2):1-13; Shakin-Eshleman et al., J Biol. Chem. May 25, 1992; 267(15):10690-8; Whitt et al., Virology. December 1991; 185(2):681-8; Benmansour et al., J Virol. August 1991; 65(8):4198-203; Burger et al., J Gen Virol. February 1991; 72 (Pt 2):359-67; Dietzschold et al., J Virol. August 1990; 64(8):3804-9; Becker, Virus Genes. February 1990; 3(3):277-84; Prehaud et al., Virology. December 1989; 173(2):390-9 and Wang et al., Chin Med J (Engl). November 1989; 102(11):885-9, the disclosures of which are incorporated by reference in their entireties, may be used in the present invention.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to a rabies glycoprotein polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of a rabies glycoprotein polypeptides and functionally equivalent fragments thereof which may enhance, decrease or not significantly affect properties of the polypeptides encoded thereby. These functionally equivalent variants, derivatives, and fragments display the ability to retain rabies glycoprotein activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from the WUSTL FTP site. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin &Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as (Nref−Ndif)*100/Nref, wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Nref=8; Ndif=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being-considered equal to uracil (U) in RNA sequences.

And, without undue experimentation, the skilled artisan can consult with many other programs or references for determining percent homology.

The invention further encompasses a rabies glycoprotein contained in a vector molecule or an expression vector and operably linked to an enhancer and/or a promoter element if necessary. In an advantageous embodiment, the promoter is a cytomegalovirus (CMV) promoter. In another embodiment, the enhancers and/or promoters include various cell or tissue specific promoters, various viral promoters and enhancers and various rabies glycoprotein DNA sequences isogenically specific for each animal species.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of rabies glycoprotein are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. rabies glycoprotein, advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Feigner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-rabies glycoprotein proteins or fragments thereof, e.g., non-rabies glycoprotein proteins or fragments thereof, cytokines, etc. to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of a rabies glycoprotein polynucleotides and, advantageously, the vector contains and expresses a polynucleotide that includes, consists essentially of, or consists of a coding region encoding rabies glycoprotein, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of rabies glycoprotein or a fragment thereof.

According to another embodiment, the vector or vectors in the preparation comprise, or consist essentially of, or consist of polynucleotide(s) encoding one or more proteins or fragment(s) thereof of rabies glycoprotein, the vector or vectors have express of the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different rabies glycoprotein isolates encoding the same proteins and/or for different proteins, but advantageously for the same proteins. As to preparations containing one or more vectors containing, consisting essentially of or consisting of polynucleotides encoding, and advantageously expressing, advantageously in vivo, rabies glycoprotein, or an epitope thereof, it is advantageous that the expression products be from two, three or more different rabies glycoprotein isolates, advantageously strains. The invention is also directed at mixtures of vectors that contain, consist essentially of, or consist of coding for, and express, different rabies proteins.

In an embodiment, the vector is a viral vector, which may be a vaccinia virus vector containing the rabies glycoprotein gene. The rabies glycoprotein may be rabies glycoprotein G derived from the ERA strain. In an advantageous embodiment, the vaccinia virus can be a Copenhagen strain and/or a tk– phenotype. In a particularly advantageous embodiment, the vector is a vaccinia virus vector (Copenhagen strain and tk– phenotype) with the rabies virus glycoprotein G encoded therein, advantageously RABORAL V-RG®.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494, 807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the attenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766, 599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter 13L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Advantageously, for the vaccination of mammals the expression vector is a canarypox or a fowlpox. In this way, there can be expression of the heterologous proteins with limited or no productive replication.

According to one embodiment of the invention, the expression vector is a viral vector, in particular an in vivo expression vector. In an advantageous embodiment, the expression vector is an adenovirus vector, such as a human adenovirus (HAV) or a canine adenovirus (CAV). Advantageously, the adenovirus is a human Ad5 vector, an E1-deleted and/or disrupted adenovirus, an E3-deleted and/or disrupted adenovirus or an E1- and E3-deleted and/or disrupted adenovirus. Optionally, E4 may be deleted and/or disrupted from any of the adenoviruses described above. For example, the human Ad5 vectors expressing a rabies glycoprotein gene described in Yarosh et al. and Lutze-Wallace et al. can be used in methods of the invention (see, e.g., Yarosh et al., Vaccine. September 1996; 14(13):1257-64 and Lutze-Wallace et al., Biologicals. December 1995; 23(4):271-7).

In one embodiment the viral vector is a human adenovirus, in particular a serotype 5 adenovirus, rendered incompetent for replication by a deletion in the E1 region of the viral genome. The deleted adenovirus is propagated in E1-expressing 293 cells or PER cells, in particular PER.C6 (F. Falloux et al Human Gene Therapy 1998, 9, 1909-1917). The human adenovirus can be deleted in the E3 region eventually in combination with a deletion in the E1 region (see, e.g. J. Shriver et al. Nature, 2002, 415, 331-335, F. Graham et al Methods in Molecular Biology Vol 7: Gene Transfer and Expression Protocols Edited by E. Murray, The Human Press Inc, 1991, p 109-128; Y. Ilan et al Proc. Natl. Acad. Sci. 1997, 94, 2587-2592; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter). The CMV-IE promoter is advantageously of murine or human origin. The promoter of the elongation factor 1a can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. A poly(A) sequence and terminator sequence can be inserted downstream the polynucleotide to be expressed, e.g. a bovine growth hormone gene or a rabbit β-globin gene polyadenylation signal.

In another embodiment the viral vector is a canine adenovirus, in particular a CAV-2 (see, e.g. L. Fischer et al. Vaccine, 2002, 20, 3485-3497; U.S. Pat. Nos. 5,529,780; 5,688,920; PCT Application No. WO95/14102). For CAV, the insertion sites can be in the E3 region and/or in the region located between the E4 region and the right ITR region (see U.S. Pat. Nos. 6,090,393; 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a rabies glycoprotein variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

It is understood to one of skill in the art that conditions for culturing a host cell varies according to the particular gene and that routine experimentation is necessary at times to determine the optimal conditions for culturing rabies glycoprotein depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of rabies glycoprotein in a target cell. Determination of the therapeutically effective amount is routine experimentation for one of ordinary skill in the art. In one embodiment, the formulation comprises an expression vector comprising a polynucleotide that expresses rabies glycoprotein and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In a specific embodiment, the pharmaceutical composition is directly administered in vivo, and the encoded product is expressed by the vector in the host. The methods of in vivo delivery a vector encoding rabies glycoprotein (see, e.g., U.S. Pat. No. 6,423,693; patent publications EP 1052286, EP 1205551, U.S. patent publication 20040057941, WO 9905300 and Draghia-Akli et al., Mol. Ther. December 2002; 6(6):830-6; the disclosures of which are incorporated by reference in their entireties) can be modified to deliver a rabies glycoprotein of the present invention to a dog. The in vivo delivery of a vector encoding rabies glycoprotein described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

One skilled in the art can determine the effective plasmid dose to be used for each immunization or vaccination protocol and species from this disclosure and the knowledge in the art.

In an advantageous embodiment, the pharmaceutical and/or therapeutic compositions and/or formulations according to the invention are administered orally. In a particularly advantageous embodiment, the oral compositions are administered as a bait drop. For example, the bait drop can comprise a polymer cube (1.25 inches by 0.75 inches) that is hollow. A sachet, or plastic packet, containing the rabies vaccine can be inserted into the hollow area of the bait and sealed with wax. The bait is attractive to raccoons and other wildlife, and strong enough to withstand distribution from airplanes flying at low altitude (e.g., about 500 feet). When a raccoon or other wildlife finds the bait and bites into it, the sachet ruptures, allowing the vaccine to enter the raccoon's mouth. Raccoons and other wildlife then become vaccinated against rabies by this oral route.

Also in connection with such a therapeutic composition, from the disclosure herein and the knowledge in the art, the skilled artisan can determine the number of administrations, the administration route, and the doses to be used for each injection protocol, without any undue experimentation.

In some embodiments, non-ionic hydrophilic surfactants having a high hydrophilic-lipophilic balance (HLB) value may be added to the disclosed formulations. This group comprises ethoxylated fatty acid monoesters of sorbitan (in particular 20 ethoxyl groups) (e.g. ethoxylated sorbitan monolaurate such as TWEEN 20®, ethoxylated sorbitan monopalmitate such as TWEEN 40®, ethoxylated sorbitan monostearate (such as TWEEN 60®, ethoxylated sorbitan monooleate such as TWEEN 80®, ethoxylated fatty alcohols (in particular 15-30 ethoxyl groups) (e.g. BRIJ 78®, BRIJ 98®, BRIJ 721®), ethoxylated fatty acids (in particular 15-30 ethoxyl groups) (e.g. MYRJ 49®, MYRJ 51®, MYRJ 52®, MYRJ 53®), non-ionic block-copolymers (e.g. polyoxyethylene/polyoxypropylene copolymer (POE-POP), such as LUTROL F127®, LUTROL F68®), and combinations thereof.

The disclosed formulation may include fatty acid esters of sorbitan (e.g. sorbitan monolaurate, like SPAN 20®, sorbitan monopalmitate, such as SPAN 40®, sorbitan monostearate, such as SPAN 60®, sorbitan tristearate, such as SPAN 65®, sorbitan monooleate, like SPAN 80®, sorbitan trioleate, like SPAN 85®, sorbitan monoisostearate, such as ARLACEL 987®, sorbitan isostearate, such as CRILL 6®), fatty acid esters of mannide (e.g. MONTANIDE 80®, mannide monooleate (such as ARLACEL A®), mannide dioleate, mannide trioleate, mannide tetraoleate), ethoxylated fatty acid esters of mannide (2, 3 or 4 ethoxyl groups) (e.g. MONTANIDE 888®, MONTANIDE 103®, ethoxylated mannide monooleate, ethoxylated mannide dioleate, ethoxylated mannide trioleate, ethoxylated mannide tetraoleate), and combinations thereof. The fatty acid may be oleate, palmitate, stearate, isostearate, laurate and combinations thereof.

In some embodiments, oils may be added to the disclosed formulations, including mineral oils, such as paraffin oil including isoparaffinic oil and/or naphtenic oil, squalane, pristane, polyisobutene oil, hydrogenated polyisobutene oil, polydecene oil, polyisoprene oil, polyisopropene oil and the like. Such oils may, for example, be those marketed under the name "MARCOL 52®" or "MARCOL 82®" (produced by Esso, France) or "DRAKEOL 6VR®" or "DRAKEOL 5®" "DRAKEOL 7®" (produced by Penreco, USA), "CLEAROL®" (produced by Sonneborn, USA), "Paraffin Oil Codex AAB2®" (produced by Aiglon, France), BLANDOL (produced by Sonneborn, USA), ONDINA 915 (produced by Shell, UK). The oil may also be a mixture of oils comprising at least 2 oils selected among the oils described herein, and in any proportion. The mixture of oils may also comprise at least one oil selected among the oils described above and at least one vegetable oil, and this vegetable oil represents from about 0.1% to about 33% of the oily phase, preferably from about 10% to about 25% v/v. These vegetable oils are unsaturated oils rich in oleic acid that are biodegradable and preferably liquid at the storage temperature (about +4° C.) or at least make it possible to give emulsions that are liquid at this temperature. For example the vegetable oil may be groundnut oil, nut oil, sunflower oil, safflower oil, soya oil, onager oil and the like.

Generally, the present invention envisions using a viscous aqueous solution comprising a suitable veterinary or pharmaceutically acceptable vehicle, excipient, or diluent including, but not limited to, sterile water, physiological saline, glucose, buffer and the like. The vehicle, excipient or diluent may also include polyols, glucids or pH buffering agents. The vehicle, excipient or diluent may, for example, also comprise amino acids, peptides, antioxidants, bactericide, and bacteriostatic compounds.

In a particular embodiment, the formulations are suitable oral baits useful for immunizing wildlife, including raccoons, foxes, and the like.

Optionally other compounds may be added as co-adjuvants to the emulsion, including, but not limited to, alum; CpG oligonucleotides (ODN), in particular ODN 2006, 2007, 2059, or 2135 (Pontarollo R. A. et al., Vet. Immunol. Immunopath, 2002, 84: 43-59; Wernette C. M. et al., Vet. Immunol. Immunopath, 2002, 84: 223-236; Mutwiri G. et al., Vet. Immunol. Immunopath, 2003, 91: 89-103); polyA-polyU ("Vaccine Design The Subunit and Adjuvant Approach", edited by Michael F. Powell and Mark J. Newman, Pharmaceutical Biotechnology, 6: 03); dimethyldioctadecylammonium bromide (DDA) ("Vaccine Design: The Subunit and Adjuvant Approach", edited by Michael F. Powell and Mark J. Newman, Pharmaceutical Biotechnology, volume 6: 157), N,N-dioctadecyl-N',N'-bis(2-hydroxyethyl) propanediamine (such as AVRIDINE®) (Ibid, p. 148), or carbomer.

The immunogen or antigen suitable for use in the present invention may be selected from the group consisting of inactivated pathogens, attenuated pathogens, immunogenic subunits (e.g. proteins, polypeptides, peptides, epitopes, haptens), or recombinant expression vectors, including plasmids having immunogenic inserts. In one embodiment of the present invention, the immunogen is an inactivated or killed microorganism.

In a preferred embodiment, the immunogen is a rabies antigen, for example the vaccinia-vectored rabies antigens of RABORAL VRG (Merial Limited).

The invention will now be further described by way of the following non-limiting examples.

EXAMPLE 1

Virucidal Activity Assay: Method for Screening Suitable Adjuvants

Prior to testing new adjuvants on animals, the inventors developed an in vitro virucidal activity assay, to make sure potential adjuvanting compounds did not have a deleterious effect on the viral-vector vaccine component. This activity assay was particularly useful for screening candidate adjuvants that could be used in formulation with vaccinia-vectored RABORAL V-RG®. Mixtures of various candidate adjuvants and RABORAL V-RG® were tested for their compatibility on Vero cells. Candidate adjuvants included CARBOPOL® and various forms of chitosan.

Viral Plaque assays were performed using Vero cell monolayers in 6-well tissue culture plates (Greiner, Monroe, N.C.). RABORAL V-RG® was obtained directly from the manufacturer, Merial, Limited (Athens, Ga., USA). Serial 1:10 dilutions of RABORAL V-RG® alone, (candidate 1 adjuvant)+RABORAL V-RG®, and (candidate 2 adjuvant)+RABORAL V-RG® were made and allowed to incubate at 37° C. for 20 min before addition to Vero cells. One hundred microliters of each dilution was plated per well in duplicate and incubated for 1 hour and 45 min at 37° C. to allow the virus to adhere to the cell monolayer. After the incubation, 2.5 ml of a 0.5% agarose overlay containing 1×RPMI, 50 μg/ml gentamycin, and 250 ng/ml amphotericin B was added over the top of the cells and the plates were returned to the incubator. After 24 hr, a second overlay was prepared as before, but with the addition of 30 μg/ml neutral red and was applied over the top of the previous overlay. The plates were monitored for plaque formation and counted 2 days after inoculation when the plaques were visible as clear spots on the plates. The reciprocal of dilutions with numbers of plaques in a countable range (between 10-100 plaques) were used to calculate viral titer as PFU/mL. It is contemplated by the inventors that candidate adjuvants with the lowest virucidal activity, as measured by this assay, should be advanced to model animal studies and/or target animal studies.

EXAMPLE 2

Chitosan Adjuvants

Chitin is a polymer that naturally occurs in crustaceans, insects, and mushrooms (Seferian, P G et al. 2001). When chitin is deacetylated, it becomes chitosan, a natural cationic polysaccharide that is highly biodegradable, has a low toxicity (Seferian, P G; Dodane, V), and has a relatively neutral pH (6.8-7.2) when combined with a phosphate buffer solution. As chitosan is neutralized, it forms a gelatinous precipitate, and its strong mucoadhesive properties increase the bioavailability of a vaccine or drug (Baudner, B C et al. 2004). In addition to acting as a thickener, chitosan is also an adjuvant. Chitosan effectively disrupts tight junctions in the mucosa, enhancing transport and absorption of drugs and vaccines across the epithelial barrier (Van der Lubben, I M et al.; Smith, J et al.; Van der Merwe, S M et al.). After crossing the epithelium, chitosan stimulates immunity by activating macrophages and cytotoxic T-lymphocytes (van der Lubben, I M et al. 2001). Chitosan is essentially non-lethal to animals as its 50% lethal dose (LD50) when given orally to mice was 16 g/kg, a LD50 lower than sucrose (Arai, K et al.; Dodane, V et al.).

Other variants of chitosan are known in the art, including TMC, a chitosan derivative that exhibits similar utility as a thickener and drug/vaccine adjuvant (Van der Merwe et al., SM; LueBen, H L et al.; Van der Lubben, I M et al., 2001). TMC is more soluble at neutral pH than chitosan (Kotze A F et al. 1997) but maintains the immunogenic and adhesive properties of chitosan; thus suggesting that this compound may be superior to chitosan under physiologic conditions.

Methods. TMC was produced from commercially available chitosan (Sigma Aldrich, St. Louis, Mo., USA) using an emulsion of 2% chitosan and 2% acetic acid. The pH of the emulsion was neutralized with NaOH and the preparation was then dried. The resulting paste was used directly to formulate solutions for this study. Stock solutions of TMC and chitosan were made with RPMI (Sigma, St. Louis, Mo.) as the diluent. The TMC solution was made to a stock concentration of 5%. The limited solubility of chitosan dictated the concentration of the solution, so the stock concentration for chitosan was 1%. To get chitosan to dissolve, HCl was added dropwise to make a more acidic solution as the mixture was stirred until the chitosan was no longer visible. After the solutions were made, they were sterilized by autoclaving to eliminate contamination that could interfere with the in vitro assays (described above) and/or interfere with immunization.

Because the effect of chitosan and TMC on RABORAL V-RG® vaccinia vector viability was unknown, mixtures of RABORAL V-RG® combined with chitosan or TMC were tested according to the method of Example 1 to determine whether the viability of the virus was affected directly by these compounds. Chitosan was prepared as a 1% stock solution and TMC was prepared as a 5% stock solution. RABORAL V-RG® suspension was mixed in equal volumes with RPMI (control), TMC or chitosan as planned for the in vivo study. Final concentrations tested ranged from 0.25%-0.5% for chitosan and 0.05%-2.5% for TMC. According to the results summarized in Table 1, the final vaccine titer was for RABORAL V-RG® alone was similar to the titer obtained when RABORAL V-RG® was combined with either chitosan or TMC.

TABLE 1

Plaque assay evaluation of RABORAL V-RG ® viability when combined with adjuvants.

| Formulation name | Volume RABORAL V-RGO ®≠ (mL) | Volume of adjuvant stock* (mL) | Final titer RABORAL V-RG ® (TCID50) | Final concentration mucosal adjuvant (%) |
|---|---|---|---|---|
| RABORAL V-RG ® | 2 | 0 | 107.7 | 0 |
| RABORAL V-RG ® + chitosan | 1 | 1 | 107.4 | 0.5 |
| RABORAL V-RG ® + TMC | 1 | 1 | 107.4 | 2.5 |

≠Stock titer of RABORAL V-RG ® = 107.4 TCID50/mL

*Chitosan stock = 1% and TMC stock = 5%

EXAMPLE 2

Vaccination of Raccoons Using Chitosan-Adjuvanted Vaccinia-Vectored Rabies Vaccines RABORAL V-RG® titers were also calculated using TCID50. Briefly, Vero cells were trypsinized and counted using a hemacytometer and added to 96-well plates with 4×104 cells per well in R5 media (100 µl RPMI (Hyclone, Logan, Utah, USA) 5% fetal bovine serum (Hyclone, Logan, Utah. USA). Vero cells were incubated at 37° C. and 5% $CO2$ for 24 hr. Serial 1:10 dilutions of RABORAL V-RG®, chitosan+RABORAL V-RG®, and TMC+RABORAL V-RG® were made in R5 media and dilutions were plated at 100 µl per well in replicates of 8 wells per dilution. Results were determined by visual examination with an inverted phase contrast microscope looking for cytopathic effect (CPE) after 1 week incubation at 37° C. and 5% CO2. Any well with evidence of CPE was considered positive for infection. TCID50 titers were calculated using the Spearman-Karber formula.

TABLE 2

Final vaccine and adjuvant formulations delivered orally to raccoons

| Adjuvant | Concentration of adjuvant | Final vaccine titer (PFU) |
|---|---|---|
| None (RABORAL V-RG ® only) | | 5 × 105 |
| Chitosan | 0.5% | 7 × 105 |
| Chitosan | 0.25% | 1 × 106 |
| TMC | 2.5% | 8 × 105 |
| TMC | 0.5% | 2 × 105 |
| TMC | 0.25% | 2 × 105 |
| TMC | 0.05% | 3 × 105 |

Forty raccoons were trapped using medium sized Tomahawk® traps in Larimer County, Colo. Raccoons were individually housed in 3×3×2.5 m pens that included den boxes and enrichment structures at the USDA National Wildlife Research Center's Outdoor Animal Research Facility for the duration of the study. When accessioned into the captive population each raccoon was evaluated for health, administered anthelmintic medication, vaccinated for distemper with the GALAXY D® vaccine (Schering-Plough Animal Health Corporation, Boxmeer, The Netherlands), and an AVID microchip pit tag (Avid Identification Systems, Inc, Norco, Calif.) was placed subcutaneously between the shoulder blades. Blood was also collected at this time to confirm baseline rabies VNA titers. Raccoons were quarantined for a minimum of 14 days prior to the start of the study.

Three vaccine formulations were prepared in 2 mL dosages as follows: 2 mL RABORAL V-RG® alone, 1 mL RABORAL V-RG®+1 mL of 1% chitosan, and 1 mL RABORAL V-RG®+1 mL of 5% TMC (Table 2). Seronegative raccoons were placed into one of four treatment groups, chitosan+RABORAL V-RG® (n=12), TMC+RABORAL V-RG® (n=12), RABORAL V-RG® only (n=12), or no vaccine (n=4). After mild sedation with 10 mg/kg ketamine HCl and 2 mg/kg xylazine (Deresienski, D T et al. 1989) blood was collected from each raccoon and 2 ml of the corresponding vaccine mixture was delivered via needleless syringe into the mouth of each animal. Raccoons were able to swallow the mixture, allowing the volume of the vaccine consumed to be confirmed. The day of vaccination is considered 0 days post inoculation (dpi). On 90 dpi all raccoons received a 2 mL booster dose of the appropriate vaccine formulation or placebo vaccine delivered orally. To follow rabies VNA development, animals were anesthetized and blood was collected via venipuncture of the jugular vein on days 4, 14, 21, 28, 60, 90, 104, 126 dpi. Rabies VNA were measured by the Rapid Fluorescent Focus Inhibition Test (RFFIT) at the Centers for Disease Control and Prevention, Atlanta, Ga. Serum dilutions up to 1:56 were tested.

A summary of raccoon neutralizing antibody responses by treatment groups were compared by logistic regression with significance determined with a p-value<0.1, due to the conservative sample sizes within each treatment group. Rabies VNA were analyzed using a generalized linear model repeated measures analysis of variance, with significance accepted at alpha=0.05. All treatments and controls were compared at each time step using Tukey's Studentized Range Test.

Table 3 illustrates the number of raccoons that responded to each vaccine by producing neutralizing antibodies after the primary and boost vaccination. After the initial vaccination, 92% raccoons vaccinated with TMC+RABORAL V-RG® responded to the vaccine with rabies VNA>0.5, the threshold suggested for wild raccoons by (Moore, S M et al.). While only 66% of raccoons vaccinated with RABOARL V-RG® had rabies VNA levels>0.5. When comparing the number of raccoons that produced rabies VNA, animals inoculated with TMC+RABORAL V-RG® performed marginally better than animals inoculated with RABORAL V-RG® alone (P-value=0.066).

TABLE 3

Summary of the number of individual raccoons responding to RABORAL V-RG ® vaccine formulations.

| Treatment | # of raccoons with Rabies VNA >0.5 prior to boost at 90 days (n) | # of raccoons with Rabies VNA >0.5 after boost at 90 days (n) |
|---|---|---|
| RABORAL V-RG ® | 8 (12) | 11 (11) |
| Chitosan + RABORAL V-RG ® | 2 (12) | 5 (11) |
| TMC + RABORAL V-RG ® | 11 (12) | 12 (12) |
| No Vaccine | 0 (4) | 0 (4) |

Rabies VNA titers among the different vaccine combinations were significantly different (F 3.32=9.07, P<0.001). FIG. 3 shows the changes in average rabies VNA titers over the course of the study. The chitosan+RABORAL V-RG® vaccine was consistently less effective at eliciting a humoral immune response than the RABORAL V-RG® vaccine and TMC+RABORAL V-RG® vaccine Tukey's Studentized Range Test demonstrated that after 60 dpi, rabies VNA responses from raccoons receiving TMC+RABORAL V-RG® were consistently higher than the raccoons that received chitosan+RABORAL V-RG®, but not significantly different than the RABORAL V-RG® only treatment group (FIG. 3).

These data present for the first time evidence that mucosal adjuvants being successfully applied to veterinary vaccine formulations. Surprising trimethylated chitosan (TMC) significantly outperformed chitosan as an effective adjuvant for RABORAL V-RG®, though both appeared to exert useful adjuvanting effects. After a dose of chitosan+RABORAL V-RG® only 16.7% of individuals produced rabies VNA and even after a booster vaccination with the same mixture only 45.5% of raccoons had detectable rabies VNA. One dose of the traditional RABORAL V-RG® formulation was enough to produce rabies VNA in 66.7% (8/12) of individuals and after a booster vaccination rabies VNA titers were detected in 100% (12/12) raccoons. However, for wildlife oral rabies vaccination (ORV) campaigns, booster vaccinations are not always possible. Because a single dose of TMC+RABORAL V-RG® mixture surprisingly induced detectable rabies VNA in 92% (11/12) of tested raccoons, the adjuvanted vaccine baits described herein should effectively compensate for the lack of ability to consistently deliver a booster dose to all wildlife animals.

TMC also altered the physical properties of the vaccine, which may be very important when designing ORV programs for raccoons. TMC produced a viscous vaccine mixture that may help prevent vaccine spillage in the field. One reason RABORAL V-RG® may be more effective in foxes and coyotes than raccoons could be the way different species handle the baits. For instance, foxes and coyotes tend to pick up a compete bait with their mouth, and masticate the bait, thus releasing the entire dose of vaccine into their mouths. Contrary to this feeding strategy raccoons tend to grasp the vaccine sachet on the ground and bite only small portions at a time, allowing the open sachet to leak, and vaccine spillage to occur (B. Schmidt unpublished data). Pen trials using placebo liquids contained in baits and sachets repeatedly show raccoons spilling>50% of the liquid contents of the sachet and the same has been documented in skunks (Grosenbaugh, D A et al. 2007; Jojola, S M et al. 2007). When volumes nearing 50% of the contents of the sachet are spilled the likelihood of successful vaccination is greatly decreased. While not yet evaluated in the field, the viscosity that TMC adds to the traditional RABORAL V-RG® vaccine may prevent or reduce spillage and increase the likelihood that a raccoons will consume the entire dose of vaccine.

The instant disclosure provides strong evidence of TMC's ability to improve the immunogenic effects of RABORAL V-RG® using only ½ of the traditional RABORAL V-RG® vaccine dose while creating a more viscous suspension, which may result in significant improvement in the vaccination of animals, including raccoons, in the field. Improvements in the delivery and immunogenicity of RABORAL V-RG® to certain wildlife species is crucial since obtaining a threshold affect for herd immunity is necessary to curtail the spread of rabies in wildlife reservoirs.

REFERENCES

WHO. Rabies vaccines: WHO position paper. Weekly epidemiological record. No. 32, 2010; 85. p. 209-320.

Hethcote, H W. An immunization model for a heterogeneous population. Theoretical Population Biology 1978; 14:338-349.

Slate, D., Algeo, TP, Nelson, K M, et al. Oral rabies vaccination in north America: opportunities, complexities, and challenges. PLOS 2009; 3(13)1-9, e529.

Fearneyhough M G, Wilson P J, Clark K A, et al. Results of an oral rabies vaccination program for coyotes. Journal of the American Veterinary Medical Association 1998; 212(4): 498-502.

Sidwa T J, Wilson P J, Moore, G M, et al. Evaluation of oral rabies vaccination programs for control of rabies epizootics in coyotes and gray foxes: 1995-2003. Journal of the American Veterinary Medical Association 2005; 227(5): 785-792.

Grosenbaugh, DA, Maki, J L, Ruppercht C E, Wall D K. Rabies challenge of captive striped skunks (*Mephitis* mephitis) following oral administration of a live vaccinia-vectored rabies vaccine. Journal of Wildlife Diseases 2007; 42(1) 124-128.

Jojola, S M, Robinson, S J, Vercauteren, K C. Oral rabies vaccine (ORV) bait uptake by captive skunks. Journal of Wildlife Disease 2007; 42(1): 97-106.

Schijns V E. Immunological concepts of vaccine adjuvant activity. Current Opinions in Immunology 2000; 12(4): 456-463.

Seferian, PG, Martinez, ML. Immune stimulating activity of two new chitosan containing adjuvant formulations. Vaccine 2001; 19:661-668.

Dodane V., Amin Kahn M., Merwin, J. R. Effect of chitosan on epithelial permeability and structure. International Journal of Pharmaceutics 1999; 182:21-32.

Baudner, BC, Verhoef, JC, Junginger, H E, et al. Mucosal adjuvants and delivery systems for oral and nasal vaccination. Drugs of the Future 2004; 29(7): 721-732.

van der Lubben, 1M, Verhoef, JC, Borchard, G., et al., Chitosan for mucosal vaccination. Advanced Drug Delivery Reviews 2001; 52: 139-144.

Smith, J., Wood, E., Dornish, M. Effect of chitosan on epithelial cell tight junctions. Pharmaceutical Research 2004; 21(1):43-49.

van der Merwe S M, Verhoef, JC, Vergeijden, JH M, et al. Trimethylated chitosan as polymeric absorption enhancer for improved peroral delivery of peptide drugs. European Journal of Pharmaceutical Sciences 2004; 58: 225-235.

Arai, K, Kinumaki, T, Fujita, T. Toxicity of chitosan. Bull. Tokai. Region Fish. Res. Lab. 1968; 56:89-94.

Dodane V., Vilivalam, VD. Pharmaceutical applications of chitosan. PSIT 1998; 1(16):246-253.

LueBen, HL, de Leeuw, BJ, Langemeyer, MWE., et al. Mucoadhesive polymers in peroral peptide drug delivery. VI. Carbomer and chitosan improve the intestinal absorption of the peptide drug buserelin. Pharmaceutical Research 1996; 13(11): 1668-1672.

van der Lubben, I M, Verhoef, JC, Borchard, G., et al. Chitosan and its derivatives in mucosal drugs and vaccine delivery. European Journal of Pharmaceutical Sciences 2001; 14:201-207.

Kotze A F, LueBen HL, de Leeuw, B J, et al. N-trimethyl chitosan chloride as a potential absorption enhancer across mucosal surfaces: In vitro evaluation in intestinal epithelial cells (Caco-2). Pharmaceutical research 1997; 14(9): 1197-1202.

Deresienski, DT, Rupprecht, CE. Yohimbine reversal of ketamine-xylazine immobilization of raccoons (*Procyon lotor*); Journal of Wildlife Diseases, 1989, 25(2):169-174.

Moore, S M, Hanlon, C A. Rabies specific antibodies: Measuring surrogates of protection against fatal disease. PLOS Neg Trop Dis 2010. 4(3)e595.

Brown, LJ, R. C. Rosatte, R C, Fehlner-Gardiner C, et al. Journal of Wildlife Diseases 2011; 47(1):182-194.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A single-dose adjuvanted Rabies virus vaccine composition consisting essentially of an attenuated recombinant Orthopox or Avipox viral vector and a trimethylated chitosan (TMC) adjuvant, wherein the vector expresses in an animal host a full-length G protein from the ERA Rabies virus strain; and wherein the TMC is present in an amount at about 2.5% w/v;

wherein the presence of the adjuvant is associated with both increased viscosity and increased protective efficacy against subsequent experimental or natural challenge with virulent Rabies virus, as compared to an otherwise equivalent composition, wherein the adjuvant has been omitted; and wherein the single-dose elicits in at least 90% of the animals protective levels of Rabies virus specific neutralizing antibodies within 90 days of administration of the single-dose composition.

2. The composition of claim 1, which is an oral vaccine.

3. The composition of claim 2, wherein the vector is an Avipox virus.

4. The composition of claim 1, wherein the vector is a Vaccinia virus.

5. A method of eliciting a protective immune response against Rabies virus in an animal comprising administering a single dose of the composition of claim 1 to said animal in an amount effective for eliciting a protective immune response in the animal.

6. The method of claim 5, wherein the vector comprises an attenuated vaccinia virus.

7. The method of claim 6, wherein the vaccinia virus is a Copenhagen strain.

8. The method of claim 6, wherein the vaccinia virus has a tk– phenotype.

9. The method of claim 6, wherein the vaccinia virus is a Copenhagen strain and has a tk– phenotype.

10. The method of claim 5, wherein the administration is oral.

11. The method of claim 10, wherein the oral administration is by a bait drop.

12. The method of any one of claims 6, 7-9, 10, or 11, wherein the animal is a raccoon.

* * * * *